United States Patent [19]

Fogwell

[11] Patent Number: 4,610,687
[45] Date of Patent: Sep. 9, 1986

[54] METHOD FOR BREEDING CONTROL IN FEMALE BOVINES

[75] Inventor: Ralph L. Fogwell, Bath, Mich.

[73] Assignee: Board of Trustees Operating Michigan State University, East Lansing, Mich.

[21] Appl. No.: 638,044

[22] Filed: Aug. 6, 1984

[51] Int. Cl.[4] .................. A61K 9/22; A61K 31/557
[52] U.S. Cl. ........................... 604/891; 604/55; 514/169; 514/170; 514/173; 514/841
[58] Field of Search ............ 514/173, 170, 169, 841; 604/890, 891

[56] References Cited

U.S. PATENT DOCUMENTS

| | | | |
|---|---|---|---|
| 2,589,898 | 3/1952 | Turner | 514/170 |
| 3,409,721 | 11/1968 | Applezweig | 514/170 |
| 3,535,419 | 10/1970 | Siegrist et al. | 514/178 |
| 3,795,734 | 3/1974 | Rochefort | 514/169 |
| 3,892,855 | 7/1975 | Short | 514/173 |
| 3,942,641 | 3/1976 | Segre | 514/170 |
| 3,957,982 | 5/1976 | Lachnit-Fixson et al. | 514/170 |
| 3,969,502 | 7/1976 | Lachnit-Fixson | 514/170 |
| 4,014,988 | 3/1977 | Pharriss et al. | 514/178 |
| 4,018,919 | 4/1977 | Black | 514/178 |
| 4,372,951 | 2/1983 | Vorys | 514/170 |

Primary Examiner—Ronald W. Griffin
Attorney, Agent, or Firm—Ian C. McLeod

[57] ABSTRACT

A method for reducing the time to estrus onset and duration of estrus in female bovines, is described. The method involves a sustained low level release of progestin over time with injection of a luteolytic agent, particularly a prostaglandin, towards the end of the time such that there is an overlap of progestin and prostaglandin administration. The sustained release is preferably by means of a vaginal implant. The method is faster and easier to use than prior art methods.

10 Claims, 4 Drawing Figures

Hormonal profiles resulting from method proposed to precisely regulate ovulation in cattle.

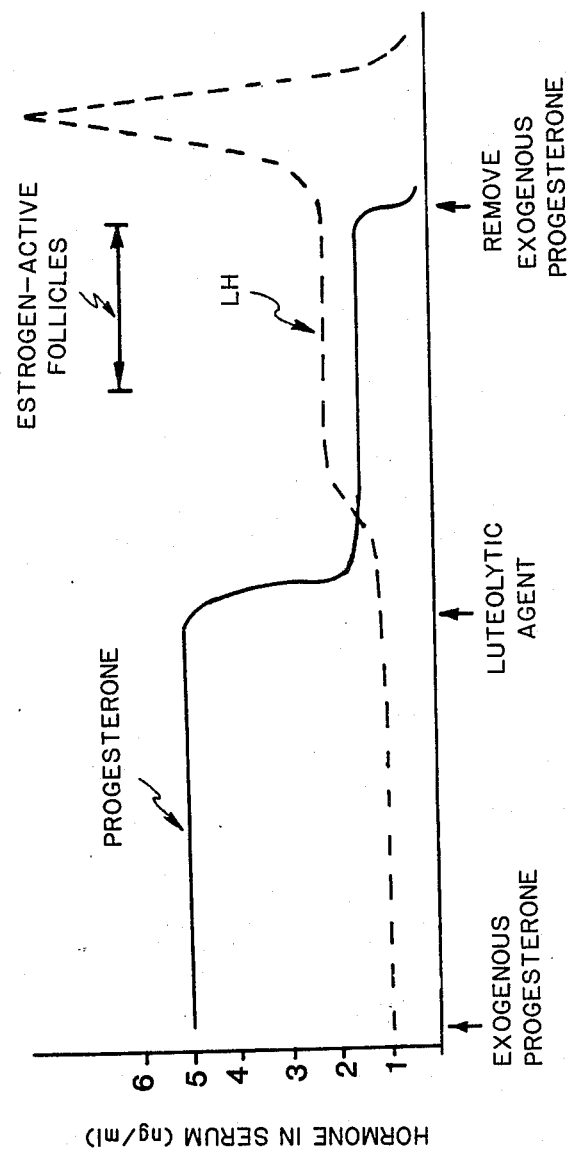
FIG. 1 Hormonal profiles resulting from method proposed to precisely regulate ovulation in cattle.

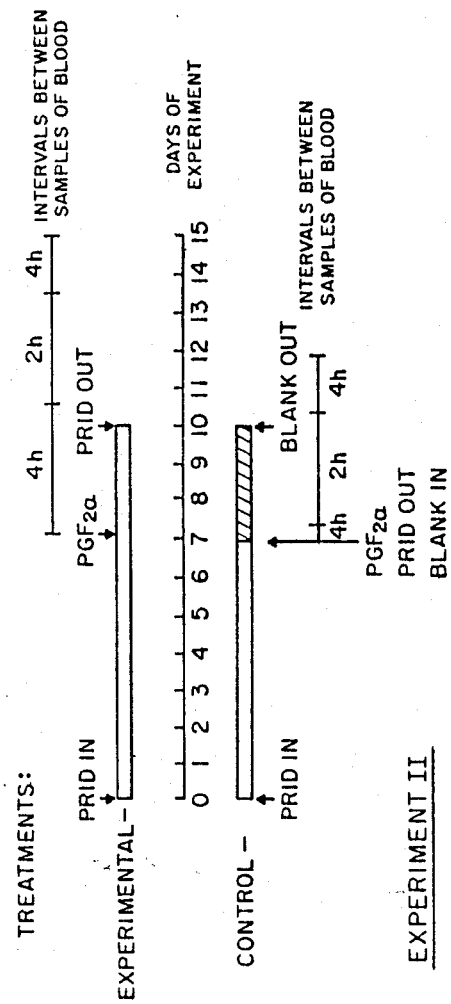

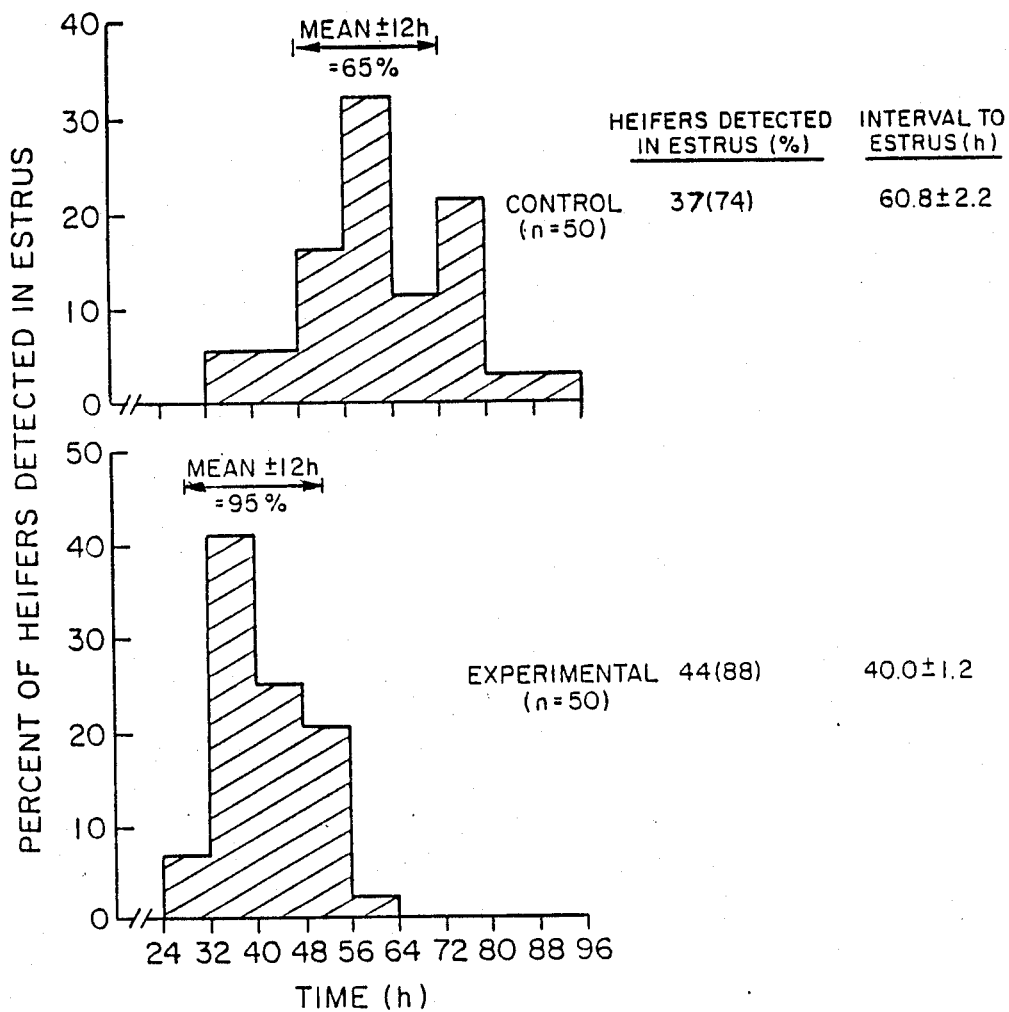

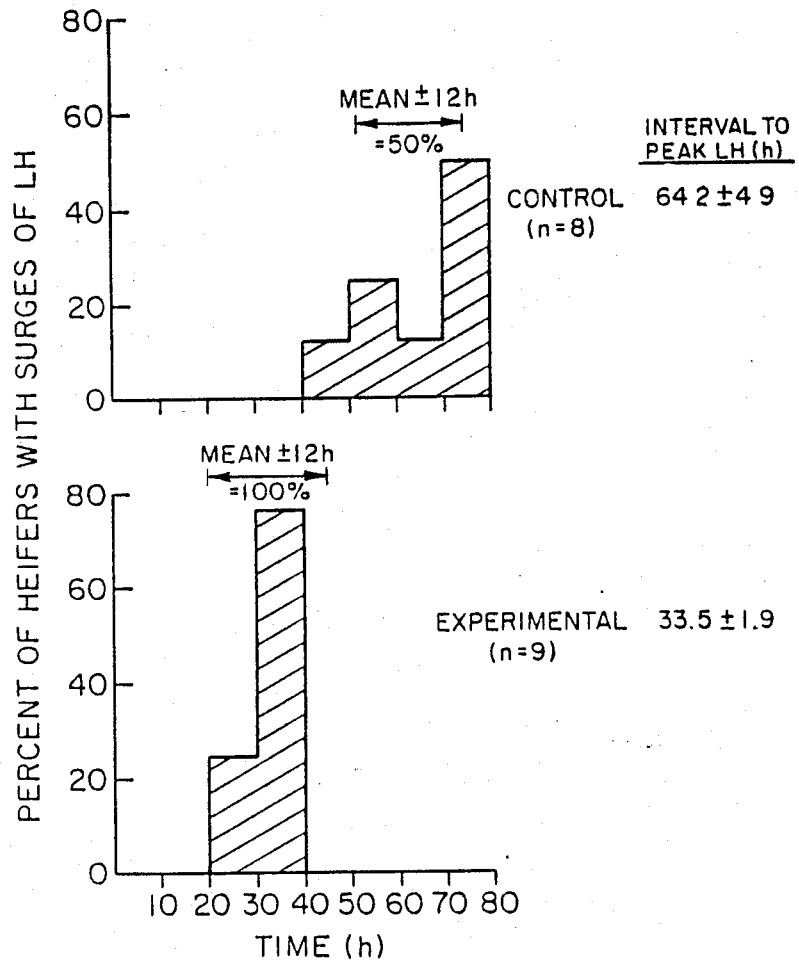

METHOD FOR BREEDING CONTROL IN FEMALE BOVINES

BACKGROUND OF THE INVENTION (1) Field of the Invention

The present invention relates to a method of fertile breeding control in female bovines by means of overlapping dosages of a progestin and a luteolytic agent using an implant for releasing low levels of the progestin over a time period into the blood stream and injection of the luteolytic agent towards the end of the period so that the progestin and agent are being administered together. In particular the present invention relates to the use of a vaginal implant for releasing the progestin over a period of time into the blood stream.

(2) Prior Art

Success of detecting cows in estrus averages 50 percent but 85 to 100 percent is possible. High success in detecting estrus requires at least four 30 minute periods of observation or 2 hours per day. Thus, low success of detecting estrus is due largely to inadequate observations of cows because labor is expensive and/or not available. Failure to observe for or detect estrus limits use and success of artificial insemination (AI). Presently AI is used on about 75 percent of dairy cattle and about 5 percent of beef cattle. Development of methods to predict estrus or ovulation would not be fruitful since this approach only addresses one animal and requires labor and management. In addition, no profound biological parameter has been identified to form a basis for a "cow-side" test of estrus/ovulation.

Methods exists to control when estrus and/or ovulation occur. Commercially available methods include:

a. Syncro-Mate B ® from CEVA (a French company)

b. Prostaglandin F$_2$ alpha and analogs
   (1) Lutalyse ® from Upjohn
   (2) Estrumate ® from Haver Lockhardt
   (3) Syncro-Cept ® from Diamond Labs.

The value of the present methods (listed above) to control estrus and/or ovulation is realized primarily through improved success of detecting estrus. However the ultimate goal of controlling ovulation is for AI to occur at a prescribed time after application of agents to control ovulation (AI by appointment) without regard for estrus. Acceptable results with "AI by appointment" will only be realized if all cattle in a group ovulate within a range of 24 hours. Present methods to control ovulation do not cause sufficient precision to warrant AI by appointment. For example, with prostaglandins, the range for occurrence of estrus or ovulation is 4 to 5 days. With Syncro-Mate B the range is 3 to 4 days. In addition to variation among individuals within a group, average intervals to estrus or ovulation are highly variable among groups of cattle, particularly when using prostaglandin.

U.S. Pat. No. 3,892,855 to Short describes the closest known prior art which uses a progestin and a luteolytic agent. In the method described in this patent, a subcutaneous progestin implant is removed at the time of injection of the luteolytic agent. The result is the onset of estrus and ovulation over a period of 1 to 5 days which is a wide time span. Further subcutaneous implants produce a risk of infection.

OBJECTS

It is therefore an object of the present invention to provide a method whereby the time interval or span of estrus is reduced to about 24 hours from about 40 hours and whereby the onset of estrus is reduced by about one-half over that obtained by termination of progestin and injection of luteolytic agent. Further it is an object of the present invention to provide a preferred method which uses a vaginal implant rather than a subcutaneous implant. Further still it is an object of the present invention to provide a method which is relatively more precise and simpler to perform than the prior art method. These and other objects will become increasingly apparent by reference to the following description and the drawings.

In the Drawings

FIG. 1 is a graph showing a hormonal profile for the method of the present invention.

FIG. 2 is a chart showing the steps in the method of the present invention.

FIG. 3 is a graph showing control and method (experimental) estrus onset after removal of an implant for progesterone.

FIG. 4 is a graph showing peaks of luteinizing hormone (LH).

GENERAL DESCRIPTION

The present invention relates to a method for fertile breeding control in female bovine comprising:

(a) establishing an estrus and ovulation blocking period of several days by continuous administering a progestin using an implant which slowly releases the progestin into the blood stream;

(b) injecting a luteolytic agent while continuing the administration of the progestin for a period of several days; and (c) terminating the administration of the progestin, thereby allowing estrus and ovulation to occur in a shorter period of time and in a relatively narrower time span than if administration of the progestin was terminated at the time of injection of the luteolytic agent. A vaginal implant is preferred because there is a more precise control over the timed release of the progestin and avoidance of infection.

SPECIFIC DESCRIPTION

The major source of variation in control of estrus/ovulation appears to be functional status of ovarian follicles. The principle of the method of the present invention is that cattle with large estrogen-producing (estrogen-active) follicles will experience estrus/ovulation sooner than cattle without estrogen-active follicles. The key to precise regulation of ovulation is to establish homogeneous follicular status (e.g. estrogen-active) among all individuals in a group of cattle.

The rationale for our approach to control status of follicles evolves from several concepts established in the literature.

a. Progesterone exerts potent negative feedback control on secretion of luteinizing hormone (LH). Within limits, this negative modulation of LH is related to dose of progesterone.

b. Growth and function of antral ovarian follicles is dependent on concentrations of LH and follicle stimulating hormone (FSH).

Our approach to precise regulation of ovulation in cattle consists of three parts: (1) exogenous progesterone to block occurrence of estrus/ovulation during the period of treatment, (2) a luteolytic agent to remove functional corpora lutea and (3) concentrations of progesterone for several days after the injection of the luteolytic agent that are low enough to allow for increased secretion of LH but no preovulatory surges of LH. These features are illustrated in FIG. 1. The preferred method to deliver progesterone is a Progesterone Releasing Intravaginal Device (PRID). This device is a coiled stainless steel strip coated with a silicone rubber (Silastic TM Dow) impregnated with progesterone in an amount of 2% progesterone based upon the weight of silicone rubber. Any other timed release composition can be used as is well known to those skilled in the art.

The key is that release of progesterone results in precise concentrations of progesterone in serum so that basal secretion of LH increases which promotes growth of estrogen-active follicles. However, no ovulations occur since preovulatory surges of LH are blocked. Thus, when PRID's are removed, all animals experience estrus, preovulatory surges of LH, and ovulation within narrow range of time (e.g. $\leq 24$ hours).

Two experiments have been conducted and represent preliminary tests of this approach. As these data are presented, heifers were treated according to sequences illustrated in FIG. 2. In contrast to experimental heifers PRID's were removed from Controls when luteolytic agent (Lutalyse ®) was injected. Thus, sustained increased secretion of LH occurred in experimental heifers but not in controls. In each instance the prostaglandin was injected into the buttocks in a saline solution. Other carriers can be used.

In both experiments reported, PRID's were 2 percent progesterone. In one experiment, we observed heifers for estrus for 30 minutes at four hour intervals and onset of estrus was first observation of standing to be mounted. Results from synchronizing heifers which were at various stages of an estrus cycle when PRID installed are presented in FIG. 3.

In a separate study we examined occurrence of preovulatory surges of LH as in indicator of ovulation (FIG. 4). Jugular blood was sampled every 2 or 4 hours for 96 hours after removal of PRID and serum was assayed for LH. From these data we identified intervals from removal of PRID to peak of preovulatory surges of LH. These heifers were synchronized with prostaglandin F$_2$ alpha before installing PRID. Thus, stage of an estrus cycle was not as variable in this study since all heifers were diestrus (FIG. 4). However, various stages of diestrus existed.

RESULTS (Experiment I):

After removal of PRID, distribution of estrus (FIG. 3) for experimental heifers was different from control heifers. Specifically for experimental heifers relative to controls, more were detected in estrus overall and more were detected in estrus during an interval of 24 ($\pm 12$) hours surrounding the respective means (FIG. 3). Therefore retention of PRID for 3 days after injecting PGF$_2$ alpha contributed to increased detection and precision of estrus in heifers.

RESULTS (Experiment II)

After removal of PRID, distribution of peaks of LH surges (FIG. 4) for experimental heifers was different from controls. Specifically, 100 percent of experimental heifers had peaks of LH surges within an interval of 24 ($\pm 12$) hours of the mean for that group. Therefore retention of PRID for 3 days after injecting PGF$_2$ alpha increased precision of preovulatory surges of LH in heifers.

CONCLUSION:

Given that greater than or equal to $\geq 95$ percent of LH surges or estrus occurred within an interval of 24 hours, maintenance of low concentrations of progesterone after injecting PGF$_2$ alpha enhances feasibility of artificial insemination at fixed time without regard for estrus.

The main objective of the method of the present invention is to increase precision of synchronizing preovulatory surges of LH (Exp. 1) and onset of estrus (Exp. 2) with a hormonal milieu of reduced progesterone and increased basal. In both experiments exogenous progesterone was administered using progesterone releasing intravaginal devices (PRID 2% Progesterone). In Exp 1, heifers received PRID for 7 days after which they all were injected with 25 mg of PGF$_2$alpha. In one group (experimental, n=9) PRID's remained in heifers for 3 days after PGF$_2$alpha. In the controls (n=8), PRIDs were removed at the time of PGF$_2$alpha. After PGF$_2$alpha, jugular blood was sampled every 4 hours for 96 hours, then every 2 hours for 72 hours and finally every 4 hours for 36 hours. Intervals from removal of PRID to peak of LH surge averaged 33.5$\pm$1.9 hours with a range of 28 to 42 hours for experimental heifers. For controls, intervals from removal of PRID to peak LH surge averaged 64.2$\pm$4.9 hours with a range of 40 to 82 hours. The intervals from removal of PRID to peak LH in experimental group were less variable (P<0.025) than in controls. In Exp. 2, heifers were assigned to experimental (n=44) and control (n=23) groups. Schedule for PRID and PGF$_2$alpha were as described in Exp. 1. After removal of PRID all heifers were observed for estrus for 30 minutes every 4 hours for 96 hours. Intervals from removal of PRID to onset of estrus (stood to be mounted) averaged 39.5$\pm$1.4 hours with a range of 24 to 56 hours for experimental heifers. For controls, intervals from removal of PRID to onset of estrus averaged 60.5$\pm$2.8 hours with a range of 36 to 60 hours. The intervals from removal of PRID to onset of estrus were less variable (P<0.025) for experimental than for control heifers. Retention of PRIDs in heifers for 3 days after PGF$_2$alpha increases synchrony of preovulatory surges of LH and onset of estrus in heifers.

The method is thus particularly adapted for establishing the onset of estrus in a herd or group of cattle. In general an amount of progesterone above about 2% by weight of the PRID was not effective and between 0.5 and 2% by weight was preferred. It was preferred to inject between 20 and 30 mg of the luteolytic agent after a blood level between about 1 to 2 nanograms of progesterone was reached. Generally it required at least about 5 days in order for the progesterone to be reduced to this level from an initially higher level. The injection of the luteolytic agent was effective for 1 to 6 days with continued progesterone from the PRID before removal.

I claim:

1. A method for fertile breeding control in female bovines comprising:
    (a) establishing an estrus and ovulation blocking period of several days by continuous administrating of a progestin using an implant which slowly releases the progestin into the blood stream;

(b) injecting a luteolytic agent while continuing the administration of the progestin for a period of 1 to 6 days; and (c) terminating the administration of the progestin, thereby allowing estrus and ovulation to occur in a shorter time period and in a relatively narrower time span than if administration of the progestin was terminated at the time of injection of the luteolytic agent.

2. The method of claim 1 wherein the progestin is progesterone.

3. The method of claim 2 wherein the progesterone is naturally occurring.

4. The method of claim 2 wherein the progesterone in the blood stream during and after injecting the luteolytic agent is between 1 to 2 nanograms per ml for at least about 1 day.

5. The method of claim 1 wherein the luteolytic agent is a prostaglandin.

6. The method of claim 5 wherein the prostaglandin is $PGF_2alpha$.

7. The method of claim 1 wherein the progestin is released by means of a vaginal implant which provides a timed release of the progestin over a period of at least about 5 days prior to injecting the luteolytic agent.

8. The method of claim 1 wherein the implant is a vaginal implant which contains between about 0.5 and 2% by weight progesterone in timed release composition as the progestin and wherein the luteolytic agent is $PGF_2alpha$ which is injected in an amount of between about 20 and 30 mg into the blood stream of the bovine.

9. The method of claim 8 wherein the progesterone is about 2% by weight of the implant and the luteolytic agent is about 25 mg.

10. The method of claim 1 wherein progesterone as the progestin is continuously administered for about six (6) days, prostaglandin as the luteolytic agent is injected on the sixth day, the progestin administration is continued for three (3) more days and then the administration of progestin is terminated, thereby allowing estrus and ovulation to occur.

* * * * *